United States Patent
Schulze-Ganzlin et al.

[11] Patent Number: 5,828,721
[45] Date of Patent: Oct. 27, 1998

[54] RADIATION DIAGNOSTICS INSTALLATION AND METHOD FOR PRODUCING PANORAMA TOMOGRAMS

[75] Inventors: Ulrich Schulze-Ganzlin, Lorsch; Josef Plötz, Bensheim, both of Germany

[73] Assignee: Sirona Dental Systems GmbH & Co. KG, Bensheim, Germany

[21] Appl. No.: 793,232
[22] PCT Filed: Jul. 28, 1995
[86] PCT No.: PCT/DE95/00989
§ 371 Date: Feb. 7, 1997
§ 102(e) Date: Feb. 7, 1997
[87] PCT Pub. No.: WO96/04849
PCT Pub. Date: Feb. 22, 1996

[30] Foreign Application Priority Data
Aug. 10, 1994 [DE] Germany .......................... 44 28 331.8

[51] Int. Cl.$^6$ ..................................................... A61B 6/14
[52] U.S. Cl. .................. 378/38; 378/39; 378/40
[58] Field of Search ........................................ 378/38–40

[56] References Cited

U.S. PATENT DOCUMENTS

| | | | |
|---|---|---|---|
| 4,856,038 | 8/1989 | Guenther et al. .......................... | 378/39 |
| 4,974,243 | 11/1990 | McArdle et al. .......................... | 378/38 |
| 5,179,579 | 1/1993 | Dove et al. ............................... | 378/38 |
| 5,195,114 | 3/1993 | Sairenji et al. ........................... | 378/40 |
| 5,228,068 | 7/1993 | Mazess .................................... | 378/54 |

OTHER PUBLICATIONS

"Matching of Tomographic Slices for Interpolation," Goshtasby et al., IEEE Trans. on Med. Imaging, vol. 11, No. 4, Dec. 1992, pp. 507–516.

*Primary Examiner*—Don Wong
*Attorney, Agent, or Firm*—Hill & Simpson

[57] ABSTRACT

A radiation diagnostic installation includes a panorama scanner for tomographically scanning a subject with radiation and for generating electrical signals dependent on the radiation shadow of the subject. A signal processor includes a memory for storing the electrical signals during the tomographic scanning and a computer for calculating signals corresponding to a tomogram of the subject in a desired slice position. The computer determines the desired slice position from the calculation of individual slice positions and their evaluation, thereby enabling faster production of tomograms in a desired slice position.

8 Claims, 3 Drawing Sheets

FIG.4
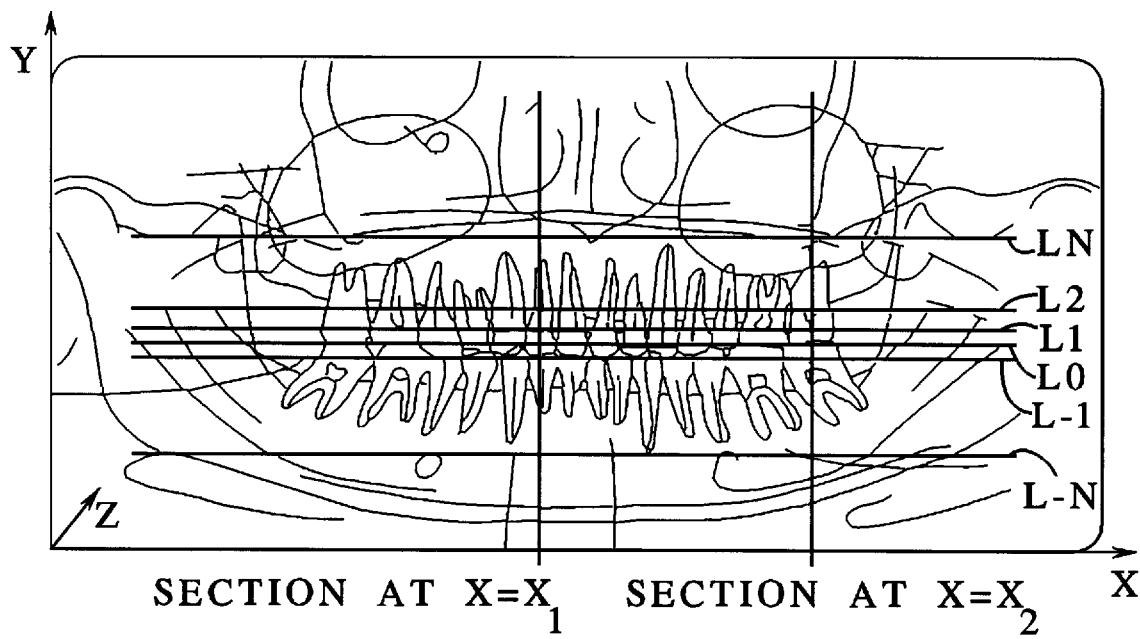
SECTION AT $X=X_1$   SECTION AT $X=X_2$
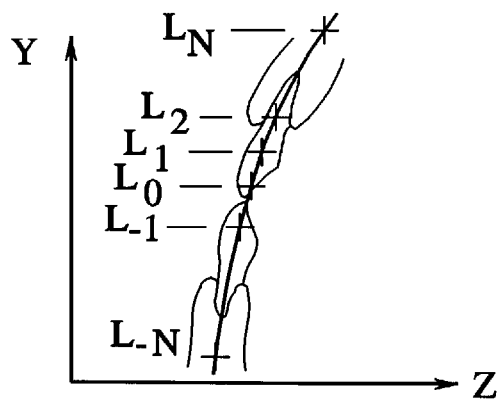
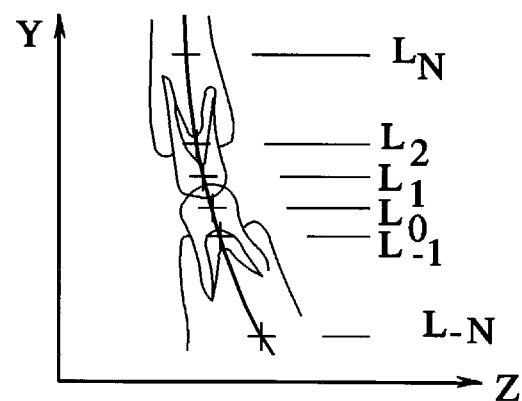
FIG.5  FIG.6

RADIATION DIAGNOSTICS INSTALLATION AND METHOD FOR PRODUCING PANORAMA TOMOGRAMS

FIELD OF THE INVENTION

The present invention is directed to a radiation diagnostic installation for producing panorama tomograms, of the type having means for tomographically scanning a subject with radiation and for generating electrical signals dependent on the radiation shadow of the subject, and having signal processing means including a memory for storing the electrical signals during the tomographic scanning and a computer for calculating signals corresponding to a tomogram of the subject in a desired slice position. The present invention is also directed to a method for producing panorama tomograms.

DESCRIPTION OF THE PRIOR ART

A radiation diagnostic installation of the above type is disclosed in German OS 41 33 066, corresponding to U.S. Pat. No. 5,195,114. This known installation has a swivel unit at which an X-ray source and an X-ray image detector are arranged lying opposite one another. The X-ray image detector acquires the X-rays that have penetrated through an exposure subject arranged between the X-ray source and the X-ray image detector. While the X-ray source and the X-ray image detector are rotated around the exposure subject, the image data received from the X-ray image detector are supplied to an image memory that sequentially stores the received image data as individual images. For producing a panorama image, an image processing means is provided that reads individual images from the image memory at predeterminable derivation intervals, shifts these by a selectable shift amount and adds the derived and the shifted individual images. The position of the tomographic image layer of a panorama image produced in this way is dependent on the interval for the derivation of the image information from the image store arrangement as well as on the amount of the shift of the image information at the point in time of the addition. A further panorama image in a further tomographic image slice can be calculated by selecting a different derivation interval and a different shift amount. In order to eliminate influences superimposed on the first panorama image that, for example, arise from an object that lies in a tomographic image slice differing from the desired tomographic image slice, it is known to calculate a second panorama image in a second image slice. The second panorama image is converted into a projected panorama image that is generated by projecting the second panorama image onto the predetermined tomographic image slice. This projected panorama image is subtracted from the first panorama image in order to obtain a panorama image that is free of these undesired effects. A clear and definite panorama image can thus be produced in the defined tomographic image slice.

Since it is not assumed that the desired image slice is directly found by entering the derivation interval and the shift amount relevant thereto, a manual approximation method is implemented by selecting different derivation intervals and shift amounts until a panorama image is calculated in a desired image slice. This manually implemented approximation method is very time-consuming. Moreover, the time required for the calculation of the panorama images is great in this approximation method. By viewing the calculated panorama images, the personnel must identify the desired image slice themselves.

SUMMARY OF THE INVENTION

It is an object of the invention to provide a radiation diagnostic installation and method wherein the time required for the determination of the desired slice position for a panorama image to be calculated is slight.

In a radiation diagnostics installation of the type initially described, this object is inventively achieved in a method and installation wherein the desired slice position is calculated in a computerized manner from the calculation of individual slice positions and their evaluation.

An advantage of the invention is that the derivation intervals and the shift amounts no longer need be manually entered, and instead the computer determines the desired, diagnostically ideal slice position of a tomogram on the basis of evaluating individual images. The time required for the production of a panorama image in the desired slice position is thus dependent essentially only on the calculating capacity of the computer and is thus reduced considerably compared to the time-consuming actions by personnel.

In an embodiment the computer calculates the desired slice position as the middle slice position between a first individual slice position and a second individual slice position, particularly when, given a dental diagnostics installation, one individual slice position is defined by the inside of the jaw or of a tooth, and the second individual slice position is defined by the outside of the jaw or of a tooth. Proceeding from the desired slice position thus identified by the computer, further slice positions, and thus panorama images of the tooth or of the jaw, can be calculated without a great expenditure of time.

In a further embodiment the computer determines the middle slice position by the calculation of individual slice positions at different locations of the subject. By joining the individual, middle slice positions, a common slice position can thus be defined that serves as starting point for the calculation of common panorama slice. This is particularly valid when the common middle slice position is matched to the mandibular arch, so that panorama images of the jaw can be produced.

In order to further reduce the time required for the production of panorama jaw exposures, in a further embodiment signals of at least one average mandibular arch are stored in a further memory, and the computer determines the middle slice position at at least three different locations of the jaw, and the desired slice position is defined by a comparison of the middle slice position to the at least one stored mandibular arch. Without a great expenditure of time, panorama exposures can thus also be produced of a jaw deviating greatly from the norm, and thus the deviation from the norm can also be identified.

DESCRIPTION OF THE DRAWINGS

FIG. 4 shows a jaw illustration in a frontal view with slices LO-LN.

FIG. 5 shows a side view of a front tooth region with slice lines LO-LN.

FIG. 6 is a side view of a molar region with slice lines LO-LN.

DESCRIPTION OF THE PREFERRED EMBODIMENTS

Figure 1:
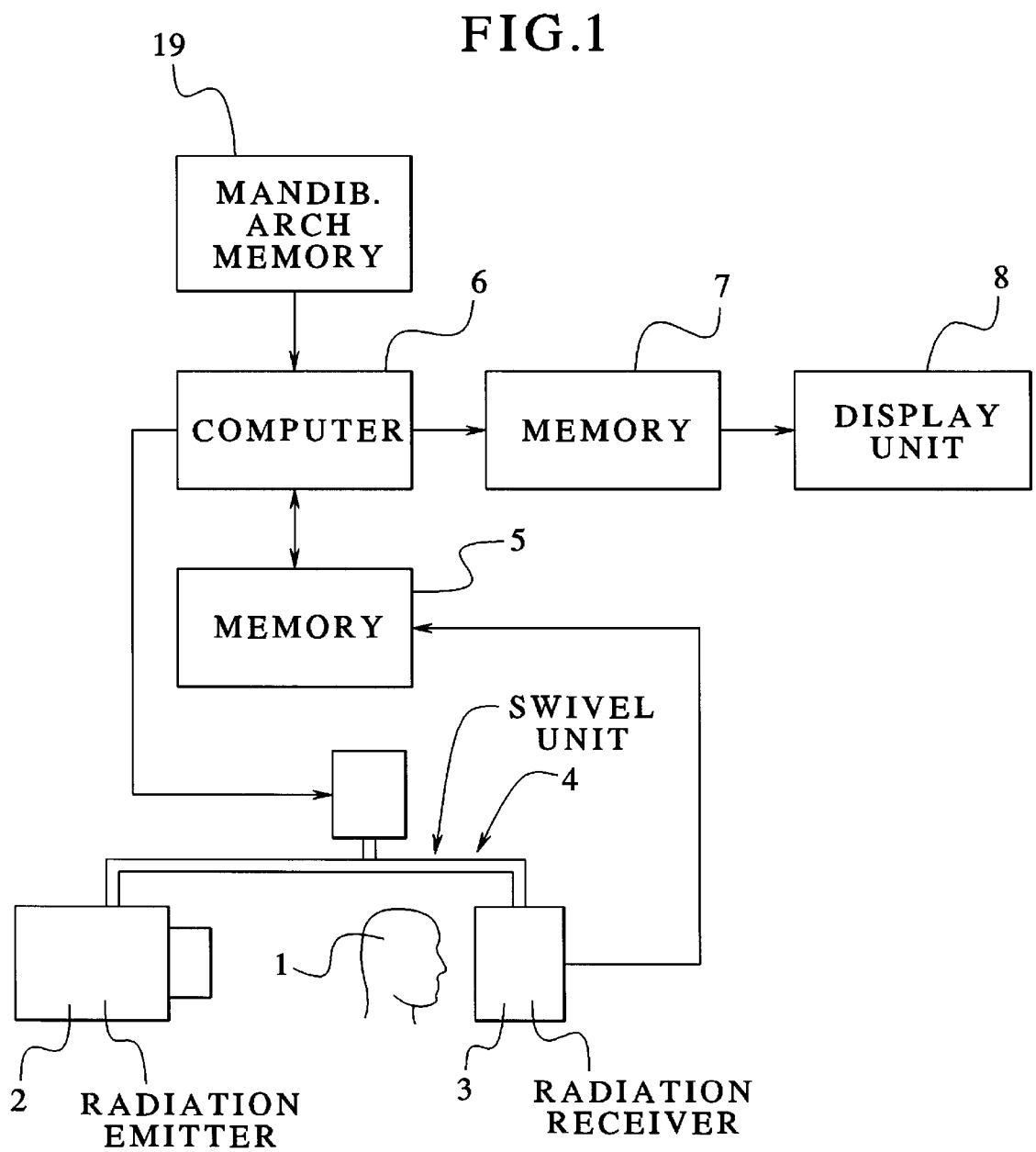
FIG. 1 is a schematic block diagram of a radiation diagnostic installation constructed and operating in accordance with the principles of the present invention.

FIG. 1 shows a radiation diagnostic installation for producing panorama tomograms. An arrangment for the tomographic scanning of a subject 1 is provided, including a radiation emitter 2 and a radiation receiver 2 that are arranged at a swivel unit 4 lying opposite one another. The radiation transmitter 2 that, for example, is implemented as an X-ray transmitter preferably emits a slit-shaped ray beam on the basis of appropriate drive and gating means, this ray beam penetrating the subject 1 and striking the radiation receiver 3 as a beam shadow of the subject 1. The radiation receiver 3 generates electrical signals that correspond to the beam shadow. To this end, the radiation receiver 3 can be implemented as an image intensifier that is followed by a video camera or an electrooptical light transducer, for example a CCD. It is likewise possible to provide a radiation transducer that directly generates corresponding electrical signals on the basis of incident radiation or that generates light that is acquired by a video camera or by a CCD converter and converted into corresponding electrical signals. During the tomographic scanning, the electrical signals are read into a memory 5 that thus contains signals corresponding to a sequence of individual images. A computer 6 is provided for controlling the swivel unit 4 and for calculating signals corresponding to a tomogram of the subject 1 in a desired slice position on the basis of the signals stored in the memory 5. The computer 6 can be followed by a second memory 7 for storing signals corresponding to at least one tomogram of the subject 1 in a desired slice position. An display unit 8 for generating a visible tomogram of the subject 1 directly follows either the computer 6 or the second memory 7.

Figure 2:
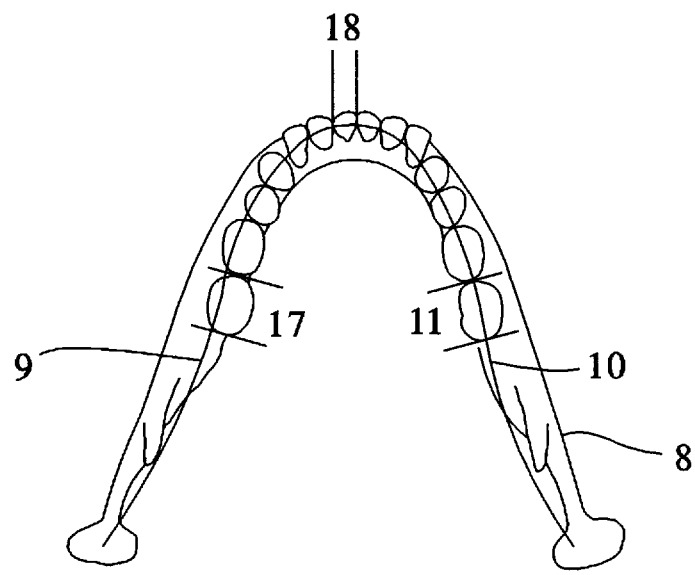
FIG. 2 shows a mandibular arch, for explaining the operation of the diagnostic installation of FIG. 1.
Figure 3:
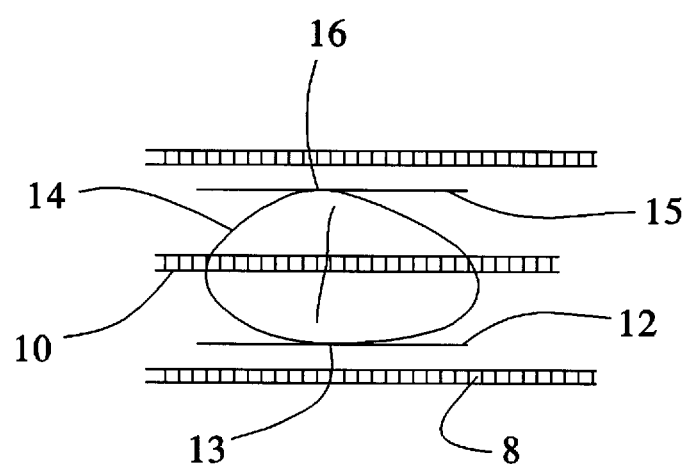
FIG. 3 shows a region of the mandibular arch of FIG. 2.

In accordance with the invention the computer 6 determines the desired slice position from the calculation of the individual slice positions and their evaluation. FIGS. 2 and 3 are referenced below for explaining the invention. FIG. 2 shows a plan view onto a jaw 8 of a subject 1. The mandibular arch is referenced 9. If this mandibular arch 9 is defined as desired slice position 10 of an individual exposure event wherein a tomogram is to be produced, then it is important to calculate this from the signals in the memory 5 without great expenditure of time. In accordance with the invention the computer 6 reads the signals from the memory 5 that correspond to a predetermined region 11 and calculates and evaluates individual slice positions. A first individual slice position 12, for example, can be defined as being tangential to the inside 13 of a tooth 14. The definition of the first individual slice position 12 can ensue by, for example, the computer 6 calculating a first tomogram of the region 11 in a first slice position and a second tomogram of the region 11 in a second slice position. On the basis of a comparison of these tomograms in view of a characteristic radiation absorption of the subject 1, the computer 6 determines whether the second slice position is located closer to the inside 13 of the tooth than the first slice position. When this is the case, then the computer 6 calculates a third tomogram of the region 11 in a third slice position and compares whether the third slice position is located closer to the inside 13 of the tooth 14 than the second slice position. This calculation is continued until the first individual slice position 12 is found. The determination of the second individual slice position 15 that is tangential to the outside 16 of the tooth 14 ensues analogously. Alternatively, first and second individual slice positions that are respectively tangential to the jaw 8 can also be calculated analogously to the above-described procedure. The above-described approximation method for defining the individual slice layers 12, 15 can be implemented not only with the computer 6 but also in combination with or by a fuzzy logic. The desired slice position 10 can be defined as a reference slice position for further slice positions, for example as the middle slice position between the first and second individual slice layers 12, 15. The calculation of the middle slice position 10 for the region 11 is less time-consuming since only the electrical signals that are allocated to the region 11 are utilized therefor. The middle slice position 10 in the further regions 17 and 18 can be calculated analogously thereto.

When a third memory 19 in which signals corresponding to a slice position of an average mandibular arch are stored is allocated to the computer 6, then the average mandibular arch can be matched to the mandibular arch of the subject 1 over the entire length of the jaw 8 on the basis of the middle slice position 10 in at least two, preferably three regions 11, 17 and 18 and, thus, the desired slice position 10 can be defined. Within the scope of the invention, signals corresponding to a plurality of slice positions can also be stored in the memory 19 and can be stored therein dependent on age, sex, size and facial type.

Alternatively, the desired slice position 10 can also be determined, by the computer calculating to the root tip and/or nerve channel (instead of relative to the tangent) of one or more teeth on the basis of individual tomogram calculation and comparison and thus defining the desired slice position 10.

Within the scope of the invention, the middle slice position 10 can be determined not only in three but in an arbitrary plurality of regions of the jaw 8. The desired slice position 10 can be defined by combining these individual slice positions.

For reasons of a simplified explanation, the previous explanation refers to the calculation of a desired slice position 10 that extends along the jaw, i.e. in at least an approximately horizontal direction. In fact, however, only a single slice line is thereby calculated as a one-dimensional quantity. Ideally, the middle slice line proceeds through the occlusal plane of the jaw 8 that describes the masticating surface. Proceeding from the middle slice line, further slice lines can be calculated that are offset relative to one another along the Y-direction in a three-dimensional space When the occlusal plane is defined by the X-direction and Z-direction. A two-dimensional slice surface then arises from the sum of all slice lines. It is assumed in the previous observations that all calculated slice lines have the same form and the slice surface thus formed is planar in the Y-direction, i.e. is thus essentially cylindrical.

When scanning a subject with a ray beam in panorama tomographs, the actual slice surface, however, is not always cylindrical but is often more likely to be shaped in the form of a segment of a frustum with an aperture angle of about 7°. It has proven advantageous for adaptation of such a frustum-shaped segment to the actual slice surface of the jaw 8 when the head is inclined slightly forward in the production of an X-ray exposure.

The jaw 8 itself, however, is also not arranged in a slice surface that could be exactly unrolled onto a plane. In a further generalization, one therefore also proceeds on the basis of a slice surface arched in the Y-direction as well. For obtaining such an arched slice surface, a plurality of slice lines that are offset relative to one another in the Y-direction and which assume different courses are calculated and combined, so that a slice surface is obtained therefrom that does justice to the anatomical conditions as well as possible imperfections in the subject positioning and that, for example, can be similar to the shape of a spherical segment.

As already noted regarding the calculation of the slice positions, the slice lines LO-LN can be calculated on the basis of data that are acquired in the scanning of the subject and that are evaluated by the computer in view of the radiation absorption (high, low or predetermined absorption). A pattern recognition, for example that of the absorption of teeth, of jaw substance, soft parts and air, can likewise be utilized. An individual jaw atlas in the form of a dataset is thus obtained on the basis of these data, the spatial position of the lower jaw and/or upper jaw and/or of all teeth being defined on the basis thereof.

Proceeding from a middle slice line LO in combination with slice lines corresponding to given geometries (sphere, cone, model jaw) that are stored as data in a memory, a calculation in view of a slice surface that comes as close as possible to the exposure subject can ensue within the scope of the invention.

A detailed calculation of the slice surface of the exposure subject, however, can also ensue by calculating each individual slice line LO-LN slices on the basis of the dataset, these slices then defining the actual slice surface.

On the basis of the calculation of the slice lines LO-LN, data corresponding to respectively allocated coordinates are obtained which, in combination with the derivation interval and the shift amount, allow signals to be calculated from which the desired panorama slice can be displayed on a monitor.

Although modifications and changes may be suggested by those skilled in the art, it is the intention of the inventor to embody within the patent warranted hereon all changes and modifications as reasonably and properly come within the scope of his contribution to the art.

We claim as our invention:

1. A radiation diagnostic installation for producing panorama tomograms comprising:

means for tomographically scanning a subject with penetrating radiation and for generating electrical signals dependent on a radiation shadow of said subject, said electrical signals comprising a dataset; and signal processing means, supplied with said electrical signals, including memory means for storing said dataset during tomographic scanning of said subject and computer means for calculating from said dataset a tomogram of said subject in a desired tomographic slice position, said computer means comprising means for automatically determining said desired tomographic slice position by calculating and evaluating a plurality of individual tomographic slice positions from said dataset.

2. A radiation diagnostic installation as claimed in claim 1 wherein said computer means comprises means for calculating said desired slice position as a middle slice position between first and second individual slice positions.

3. A radiation diagnostic installation as claimed in claim 2 wherein said means for tomographically scanning a subject comprises means for tomographically scanning a jaw of said subject for producing a panorama tomogram of said jaw, and wherein said first individual slice position comprises an inside of said jaw and wherein said second individual slice position comprises an outside of said jaw.

4. A radiation diagnostic installation as claimed in claim 2 wherein said means for tomographically scanning a subject comprises means for tomographically scanning a jaw of said subject for producing a panorama tomogram of said jaw, and wherein said first individual slice position comprises an inside of a tooth and wherein said second individual slice position comprises an outside of said tooth.

5. A radiation diagnostic installation as claimed in claim 2 wherein said computer means comprises means for determining said middle slice position by calculating a plurality of said individual slice positions within a region of said subject.

6. A radiation diagnostic installation as claimed in claim 2 wherein said means for tomographically scanning a subject comprises means for tomographically scanning a jaw of said subject for producing a panorama tomogram of said jaw, said radiation diagnostic installation further comprising further memory means for storing data relating to a mandibular arch, and wherein said computer means includes means for matching said middle slice position to the mandibular arch stored in said further memory means.

7. A radiation diagnostic installation as claimed in claim 6 wherein said further memory means comprises means for storing data relating to at least one average mandibular arch, wherein said computer means comprises means for determining said middle slice position in at least two different regions of said jaw of said subject, and wherein said computer means includes means for defining said desired slice position by comparing said middle slice position to said average mandibular arch stored in said further memory.

8. A method for operating a radiation diagnostic installation for producing a panorama tomogram of a subject, comprising the steps of:

tomographically scanning said subject with penetrating radiation and generating electrical signals dependent on a radiation shadow of said subject, said electrical signals comprising a dataset;

storing said dataset;

conducting an approximation for determining a desired tomographic slice position by calculating individual tomographic slice positions in a computer from said dataset and evaluating said individual tomographic slice positions; and generating a tomogram of said subject in said desired tomographic slice position from said dataset.

* * * * *